United States Patent
Bhushan

(10) Patent No.: US 9,936,902 B2
(45) Date of Patent: Apr. 10, 2018

(54) ERGONOMIC DATA COLLECTION AND ANALYSIS

(71) Applicant: The Boeing Company, Chicago, IL (US)

(72) Inventor: Anant Bhushan, Wilmington, DE (US)

(73) Assignee: The Boeing Company, Chicago, IL (US)

( * ) Notice: Subject to any disclaimer, the term of this patent is extended or adjusted under 35 U.S.C. 154(b) by 482 days.

(21) Appl. No.: 13/888,055

(22) Filed: May 6, 2013

(65) Prior Publication Data

US 2014/0326084 A1    Nov. 6, 2014

(51) Int. Cl.
*G06F 3/0488* (2013.01)
*A61B 5/11* (2006.01)
*G01L 3/26* (2006.01)

(52) U.S. Cl.
CPC .............. *A61B 5/1126* (2013.01); *A61B 5/11* (2013.01); *G01L 3/26* (2013.01)

(58) Field of Classification Search
CPC ..... G06F 3/0488; G06F 3/04883; G06F 3/044
See application file for complete search history.

(56) References Cited

U.S. PATENT DOCUMENTS

| | | | |
|---|---|---|---|
| 6,160,478 A * | 12/2000 | Jacobsen | A61B 5/0022 128/903 |
| 7,454,002 B1 | 11/2008 | Gardner et al. | |
| 7,592,997 B2 | 9/2009 | Evers-Senne et al. | |
| 8,180,591 B2 | 5/2012 | Yuen et al. | |
| 8,180,592 B2 | 5/2012 | Yuen et al. | |
| 2005/0033200 A1 * | 2/2005 | Soehren et al. | 600/595 |
| 2007/0276270 A1 | 11/2007 | Tran | |
| 2010/0023314 A1 * | 1/2010 | Hernandez-Rebollar | 704/3 |
| 2010/0063365 A1 * | 3/2010 | Pisani | A61B 5/0002 600/301 |
| 2010/0241464 A1 * | 9/2010 | Amigo | G06Q 40/08 705/4 |
| 2011/0159939 A1 * | 6/2011 | Lin et al. | 463/8 |

(Continued)

FOREIGN PATENT DOCUMENTS

| | | |
|---|---|---|
| CN | 101680802 | 3/2010 |
| DE | 102009027585 A1 | 1/2011 |

(Continued)

OTHER PUBLICATIONS

Raffler et al.; "Assessing Combined Exposures of Whole-Body Vibration and Awkward Posture—Further Results from Application of a Simultaneous Field Measurement Methodology"; Industrial Health National Institute of Occupational Safety and Heath Japan; vol. 48 No. 5; 2010; p. 638-644.

Ellegast et al; "Workload Assessment in Field Using the Ambulatory CUELA System"; Digital Human Modeling; Jul. 19, 2009; p. 221-226.

(Continued)

*Primary Examiner* — Alexander Eisen
*Assistant Examiner* — Mansour M Said
(74) *Attorney, Agent, or Firm* — Gates & Cooper LLP

(57) ABSTRACT

Techniques for monitoring and detecting ergonomic hot spots associated with movements of subjects are disclosed. For example, data may be collected by way of sensors attached to a plurality of subjects and may be analyzed to determine forces (e.g., vibration, jerks, acceleration, etc.) associated with the movements of the subjects. The analyzed data can be compared to ergonomic conditions to detect the ergonomic hot spots.

21 Claims, 6 Drawing Sheets

(56) References Cited

U.S. PATENT DOCUMENTS

| | | | |
|---|---|---|---|
| 2012/0136231 A1* | 5/2012 | Markel | A61B 5/0015 600/388 |
| 2012/0265104 A1 | 10/2012 | Menegon et al. | |
| 2013/0027341 A1* | 1/2013 | Mastandrea | G06F 3/014 345/173 |
| 2013/0046505 A1* | 2/2013 | Brunner et al. | 702/141 |
| 2013/0060168 A1 | 3/2013 | Chu et al. | |

FOREIGN PATENT DOCUMENTS

| | | |
|---|---|---|
| DE | 202011050289 U1 | 7/2012 |
| EP | 2273244 | 1/2011 |
| EP | 2273244 A2 | 1/2011 |
| WO | WO 2005/120348 A1 | 12/2005 |
| WO | WO 2008/149130 A1 | 12/2008 |

OTHER PUBLICATIONS ict-cognito.org Demonstrators. Augmented Reality Handbook (Dec. 2012, DFKI) Accessed Feb. 7, 2013 via the Internet at URL<http://www.ict-cognito.org/demo.html> 5 pages.

ict-cognito.org Cognito System. DFKI Augmented Vision © 2012. Accessed Accessed Feb. 7, 2013 via the Internet at URL <http://www.ict-cognito.org/system.html> 1 page.

Majoe, D. et al., "Ergonomic Low Cost Motion Capture for every day health exercise", IEEE, 2008, pp. 627-632.

Tino, A. et al., "Wireless Vibrotactile Feedback System for Postural Response Improvement", $33^{rd}$ Annual International Conference of the IEEE EMBS. Boston, MA. USA, Aug. 30-Sep. 3, 2011, 5203-5206.

European Patent Application No. 14158262.7; Office Action—Article 94(3); dated Dec. 3, 2015; 5 pages.

Chinese Office Action (with English translation) dated Sep. 14, 2017 for Chinese Patent Application No. 201410189746.1.

* cited by examiner

ERGONOMIC DATA COLLECTION AND ANALYSIS

FIELD

The present disclosure relates to monitoring and detecting ergonomic data associated with movements of subjects.

BACKGROUND

Workplaces and activities may require various physical movements and positions. For example, factory jobs often necessitate that a subject (e.g., a worker) perform repetitive tasks. The worker may also be required to get into various body positions and/or apply forces to certain body parts. The worker can be tasked to lift objects, assemble overhead components, and other physical tasks. Repetitive tasks can lead to physical discomfort resulting from pain, injuries, or the like and can result in lost productivity, lost revenue, added health care, and other costs.

Various ergonomics solutions can be implemented to improve comfort, health, safety, and productivity. These solutions typically involve an analysis of postures of a subject while performing tasks. For example, an ergonomist can be deployed on the factory floor to visually observe the postures to determine ergonomic conditions associated with performing the tasks and to suggest alternatives based on the ergonomic conditions. In this example, the success of the solution may be improved by providing proper training to the ergonomist and by increasing the number of deployed ergonomists.

SUMMARY

Methods, systems, and computer readable media for monitoring ergonomic data associated with the physical movements of subjects (e.g., workers at a factory, employees at a workplace, individuals performing various activities, etc.) are disclosed. The present disclosure may advantageously improve detection of ergonomic hot spots and other desired factors, allowing for proactive administrative and engineering solutions.

For example, a method for monitoring performance of a process is described. The method may comprise receiving acceleration data associated with nodes, the acceleration data being indicative of movements of the nodes, and analyzing the acceleration data by comparing the acceleration data to one or more acceleration thresholds.

In an example, a system is described. The system may include a first computing device comprising a first accelerometer, the first computing device configured to collect acceleration data caused by movements. The ergonomic system may also include a second computing device communicatively coupled to the first computing device. The second computing device may be configured to receive the acceleration data from the first computing device and process the received acceleration data to determine a relationship between the acceleration data and one or more thresholds.

In another example, a computer readable storage medium is described. The computer-readable storage medium may comprise computer readable instructions that, when executed on a system comprising a processor and memory, cause the system to at least receive data indicative of physical movements of a plurality of subjects by way of a plurality of devices attached to the plurality of subjects, and analyze at least a subset of the data by comparing the subset of the data to one or more thresholds.

The features, functions, and advantages can be achieved independently in various embodiments or may be combined in yet other embodiments, further details of which can be seen with reference to the following description and illustrations.

BRIEF DESCRIPTION OF THE DRAWINGS

Embodiments of techniques in accordance with the present disclosure are described in detail below with reference to the following illustrations.

DESCRIPTION

Figure 1:
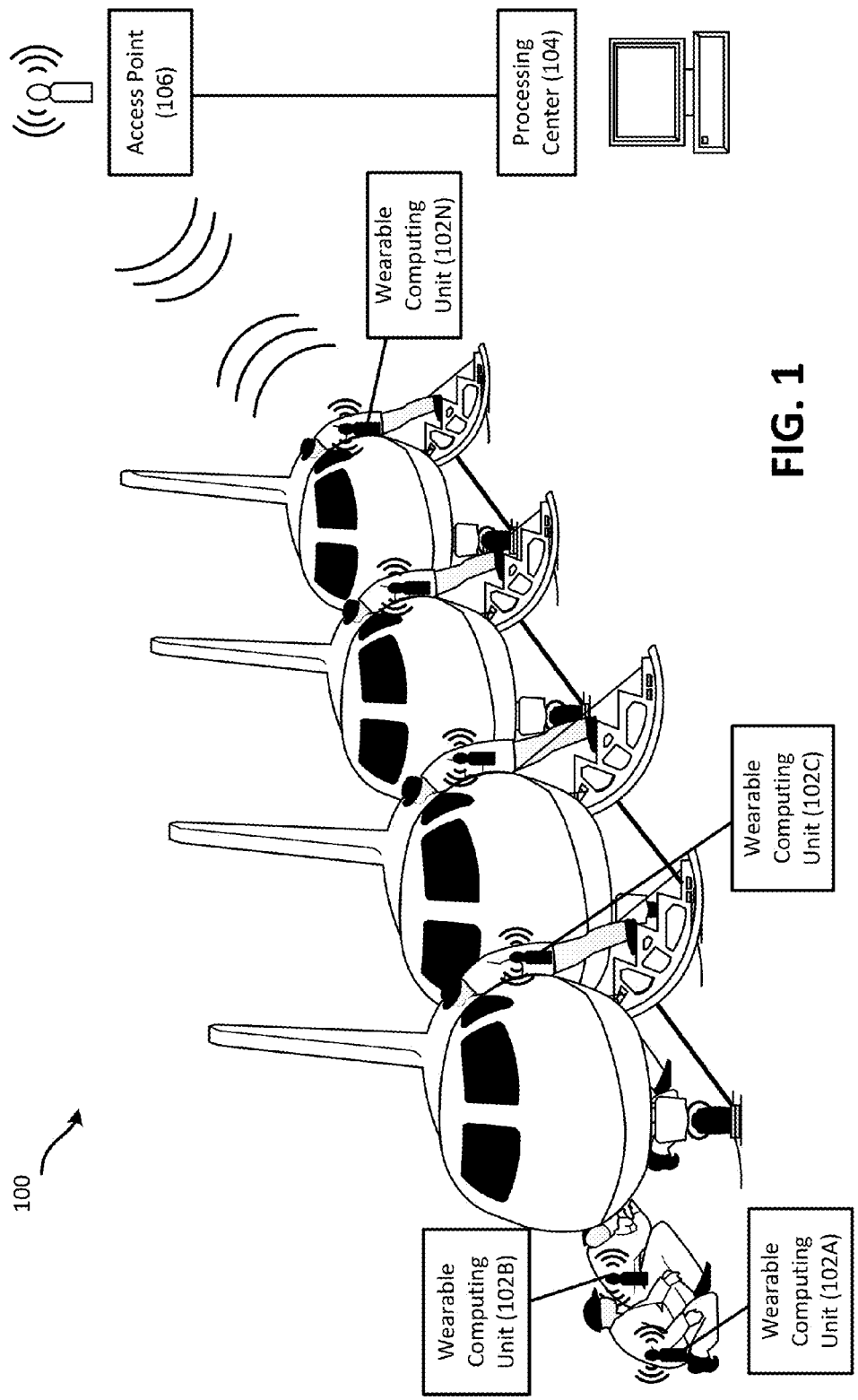
FIG. 1 is an illustration of an example computing system for monitoring and improving ergonomic conditions associated with an environment in accordance with the disclosure.

Computing system-assisted ergonomics systems may be used to analyze work and other environments. For example, a computing system can include position sensors that are attached to the subject's body to determine the posture based on the positions of body parts. These positions are compared using a standard ergonomic evaluation method, e.g., a Rapid Upper Limb Assessment (RULA) chart, to determine an ergonomic score for the posture. As such, the computing system provides the subject with real-time information about his or her posture by way of the ergonomic score and suggests changes to reduce posture-related physical discomfort.

Techniques for monitoring movements and improving ergonomic conditions associated with an environment are described herein and are based on industry acceptable and unacceptable practices. These techniques may include collecting data associated with a subject and related to a combination of factors (e.g., human factors such as postures of the subject, forces applied to the subject, or the like). The subject may be a person, such as a worker performing tasks within a certain work environment, a person participating in a gaming environment, an athlete in a sporting environment, or the like. The subject may also be non-human, such a robot or a machine configured to simulate movements and positions that may be undertaken by a person. Additionally, the collected data may be analyzed to determine the ergonomic conditions. This determination may include a correlation between the combination of human factors and a reference such as a condition or an activity. For example, data related to movements of an employee may be collected and analyzed to determine whether the employee has engaged in a physical activity of interest. The techniques may allow a third party (e.g., an ergonomist) to use the collected data to provide a solution that encourages or discourages the activity of interest based on, for example, whether the activity of interest is desirable.

Specific details of examples of the present disclosure are set forth in the following description and in FIGS. 1 through 6. The various techniques described herein can be implemented in hardware, software, or a combination thereof. In the figures, similar symbols identify similar components, unless context dictates otherwise. Certain well-known technology details, such as computing and software technologies, are not set forth in the following description to avoid unnecessarily obscuring the various examples. Those of ordinary skill in the relevant art will understand that they can practice other examples of the disclosure without departing from the scope of the subject matter presented herein.

Generally, the techniques described herein allow for comparison between the collected data and one or more references which may provide opportunities to improve aspects of the environment. For example, these techniques may allow for improvements to the health and safety of the environment by reducing the potential for environment-related physical discomfort (e.g., pain, injuries, etc.). A computing system may be used to monitor various ergonomic data associated with physical movements of a plurality of subjects within the environment (e.g., workers in a workplace, persons that the organization employs, contracts, or is associated with, etc.). The ergonomic data need not be limited to postures (e.g., posture data) but may include other types of data such as motion, force, vibration, velocity, acceleration, jerk, location, etc. After collecting the data (e.g., a combination of motion data, force data, vibration data, velocity data, acceleration data, jerk data, location data, etc.) from the plurality of subjects, the computing system may analyze the data to determine ergonomic hot spots within the environment. These hot spots may be associated with ergonomically unacceptable conditions that pose risks for environment-related physical discomfort to the subjects (e.g., a physical condition indicative of a risk of pain or injuries). The hot spots may include, for example, location-based (e.g., a location or an area within the environment that poses an ergonomically unacceptable condition), task-based (e.g., a job or an activity that is ergonomically unsafe to perform for a certain duration or at a certain frequency), movement-based (e.g., a movement of a subject that creates a potential for physical discomfort when repeated), or body-based hot spots (e.g., a body part that is likely to be subjected to discomfort when a task is performed under an ergonomically unacceptable condition).

In addition, the data may be analyzed to return ergonomic benefits to the subjects and to improve the health and safety of the environment. For example, various pre-discomfort solutions may be analyzed to reduce and, in some instances, eliminate the potential for the physical discomfort. The solutions can be individualized for each subject by, for example, continuously monitoring his or her task-related movements and generating an alert when a hot spot is identified. The solutions can also be customized for a group of subjects. For example, a location-based hot spot is identified where the group works, the associated location (e.g., reconfigure machinery, tools, warning signs, etc.) can be reconfigured to reduce the potential for physical discomfort to the group. These and other aspects of the present disclosure are further described herein below.

FIG. 1 illustrates a computing system 100 that the organization can implement to monitor and improve the health and safety of the environment. Although the figure uses an example of a factory floor, the computing system 100 can be implemented in other environments such as a workplace, a storage facility, a manufacturing facility, a work process, an office building, a physical or occupational therapy environment, a gaming environment, or the like. Similarly, although the figures depicts an example depicts the computing system 100 can be implemented to monitor and analyze movements of subjects, the computing system 100 can be implemented to monitor and analyze ergonomic data associated with any other subjects, such as for example, gamers, athletes, employees, etc. In a basic configuration, the computing system 100 includes a plurality of wearable computing units 102A-N attached to a plurality of subjects and in communication with a processing center 104. The wearable computing units may be referred herein singularly as "wearable computing unit 102" or in the plural as "wearable computing units 102." The wearable computing units 102 and the processing center 104 interface through an access point 106 that implements, for example, 802.11 or 802.16 wireless communication standards. Other interfaces may also be used instead and include, for example, a wired connection in the form of ports or docks at the processing center 104 to which the wearable computing units 102 connect, a proximity wireless connection that implements Bluetooth® or the like.

Each of the wearable computing units 102 is configured to be attached to a subject, to monitor and collect data indicative of his or her physical movements, and to transmit the collected data to the processing center 104. This transmission can be in real time (e.g., as soon as the data is collected and the interface to the processing center 104 is available), periodic (e.g., after a predefined duration, the data is transmitted), at intervals, or automatic when the interface is detected.

The wearable computing unit 102 can also receive a service associated with an ergonomic hot spot from the processing center 104 and can perform a specific function based on the received service. For example, if the services include instructions to alert the subject of an ergonomic hot spot, the wearable computing unit 102 triggers an alert through one of its sensory means (e.g., audible sound broadcasted over a speaker, a text alert displayed on a monitor, a flashing light emitted by a light emitting diode (LED), a vibration activated at a surface of the wearable computing unit 102, etc.). If the service includes information about an ergonomic condition, the wearable computing unit 102 processes the information to determine whether a potential for physical discomfort (e.g., an injury risk, a likelihood of feeling pain in a certain body part, etc.) exists and whether an alert should be generated.

In addition to providing the service to the wearable computing units 102 as explained above, the processing center 104 is also configured to receive, store, and process the data transmitted from the plurality of wearable computing units 102 and to identify hot spots of the environment based on the data. The processing center 104 can analyze the data in real-time or near real-time such that the provided service allows the wearable computing unit 102 to alert the worker before he or she is subject to physical discomfort.

To identify the hot spots, the processing center 104 can analyze the data received from the plurality of wearable computing units 102 against ergonomic conditions. If the analysis reveals a pattern of movements (e.g., physical movements, vibration movements, movements of body parts, etc.) indicative of an ergonomically unacceptable condition, the processing center 104 can associate the pattern with a hot spot. For example, when the analysis indicates that arms of subjects performing tasks by way of a tool at a specific location of the factory floor are subject to high vibrations, the processing center 104 identifies the specific location as a hot spot and associates it with the use of the tool. In another illustration, when the analysis indicates that a specific task requires the subjects to perform overhead motions for continuous and extended period of times, the processing center 104 identifies the specific task as a hot spot and associates it with the overhead motions.

The ergonomic conditions can be defined based on various parameters that include input at the processing center 104 received from an ergonomist (e.g., a user of the processing center 104 that is responsible for monitoring the safety of the factory floor). The input can include a history of work-related physical discomfort (e.g., a history of injuries), human factors considerations (e.g., types and frequencies of movements, movements in confined spaces, durations of movements, age of the subject, health of the subject, etc.), and/or industry acceptable and unacceptable practices (e.g., a one hundred pound object cannot be continuously lifted for more than one minute). The processing center 104 processes the input to derive requirements that specify the acceptable and unacceptable ergonomic conditions. For example, when the input describes discomfort suffered from using a tool for a period of time, the processing center 104 generates a requirement that renders a use of the tool for a duration that exceeds the period of time as an ergonomically unacceptable condition. Likewise, when the input describes an acceptable industry practice, the processing center 104 generates a requirement that renders a work condition that does not conform to this practice as an ergonomically unacceptable condition.

Further, the processing center 104 can refine these requirements based on the hot spots it identifies, such that the processes of defining the ergonomic conditions and identifying the hot spots are iterative. For example, the processing center 104 generates a requirement that renders lifting an object in excess of one hundred pounds as an ergonomically unacceptable condition and identifies the corresponding hot spots. In response, the ergonomist takes corrective actions and revises the tasks on the factory floor to avoid such lifting. In turn, the processing center 104 no longer identifies hot spots that are associated with this ergonomically unacceptable condition. Next, if a subsequent input data indicates that a worker suffered discomfort from lifting an object that weighed seventy-five pounds, the processing center 104 revises the requirement to render lifting an object in excess of seventy-five pounds as an ergonomically unacceptable condition. The processing center then analyzes new data received from the wearable computing units 102 to identify new hot spots associated with the revised condition. This iterative process can be repeated until no injuries are further recorded or based on additional input from the ergonomist.

Figure 6:
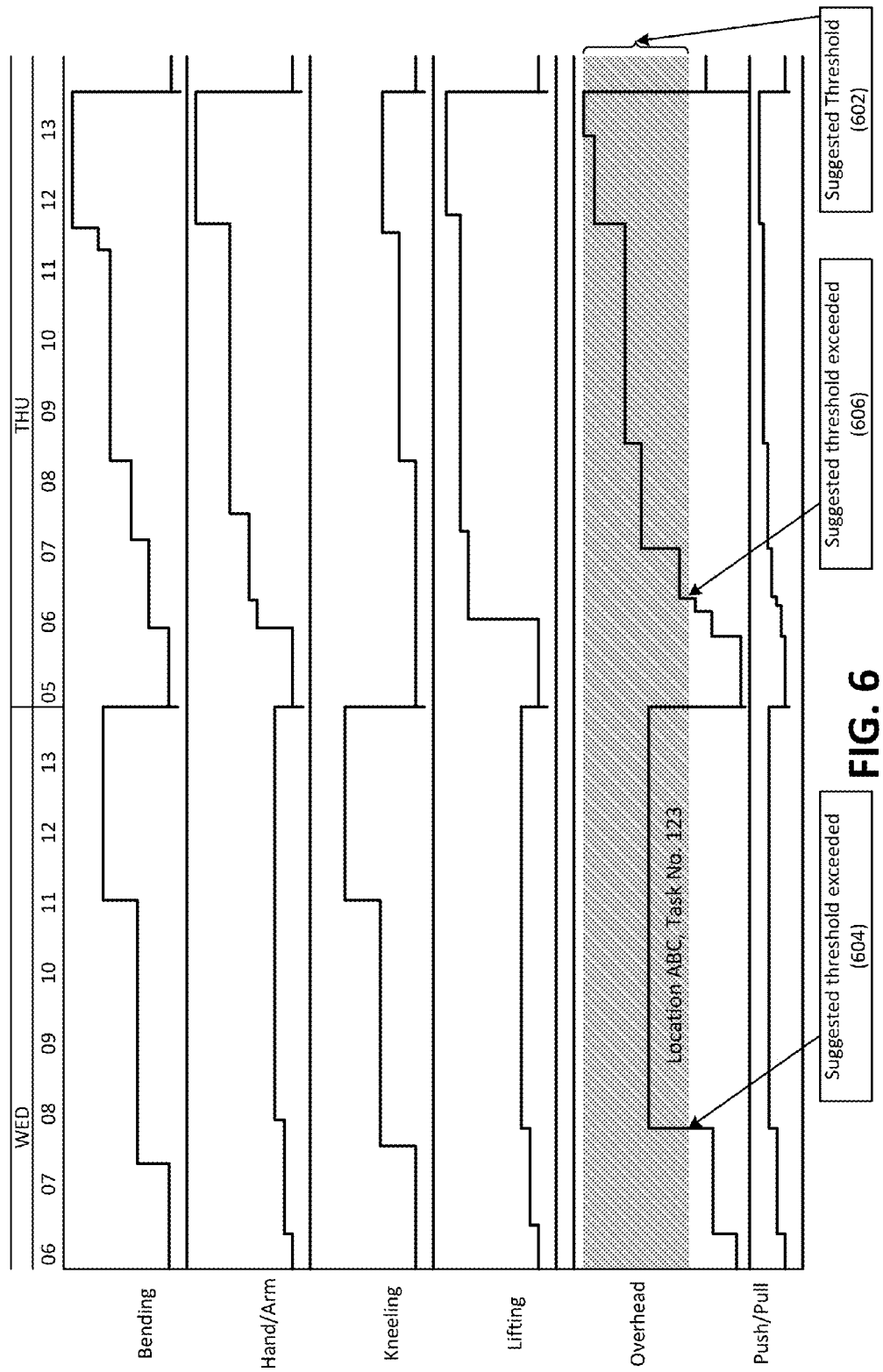
FIG. 6 is an illustration of an example tool for analyzing ergonomic data in accordance with the disclosure.

In addition to alerting subjects of hot spots and/or their potential for experiencing physical discomfort, the processing center 104 can provide analysis tools to the ergonomist to forecast these hot spots and potentials and/or to take corrective actions. An example of such tools is illustrated in FIG. 6. In an example, these tools include a visualization of the of the processing center 104's data analysis such that movements of a subject or a group of subjects are tracked over a period of time (e.g., a work shift, a day, a week, a month, etc.). The visualization can identify the movements, the associated tasks and/or locations, and any resulting hot spots. As such, the tools allow the ergonomist to perceive the hot spots, predict potential for physical discomfort that are likely to occur, and proactively execute corrective actions to avoid the physical discomfort from actually occurring. These actions may include administrative (e.g., discuss a hot spot with a worker or with a leader of a group of workers, etc.) and engineering solutions (e.g., propose a modification to the flow of a task, to the tools associated with performing the task, to the part installed by the task, etc.).

Figure 2:
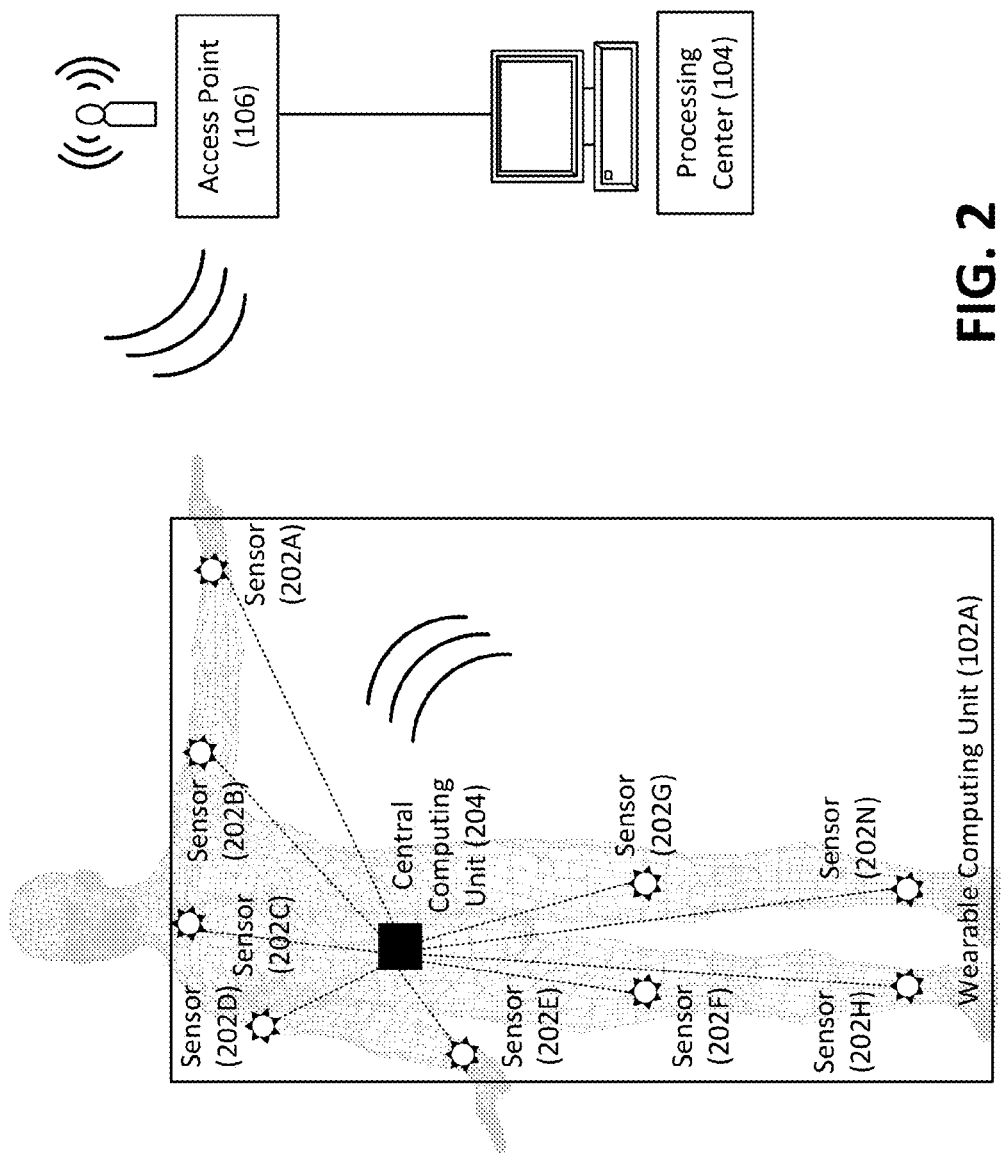
FIG. 2 is an illustration of an example computing system for collecting various ergonomic data in accordance with the disclosure.

Turning to FIG. 2, an example of a wearable computing unit 102A is illustrated. The wearable computing unit 102A is configured to be attached to a subject, to collect data associated with movements of various body parts of the subject, and to transmit the collected data to the processing center 104. In a basic configuration, the wearable computing unit 102 includes a number of sensors 202A-N (which may be referred herein singularly as "sensor 202" or in the plural as "sensors 202") connected to a central computing unit 204. The sensors 202 are configured to measure and transmit data indicative of the movements to the central computing unit 204, which in turn, processes and transmits the data to the processing center 104.

Each of the sensors 202 is typically attached to a subject's body part, which may be referred to as a node. A node is a body part that connects a peripheral of the body (e.g., hand, arm, foot, head, etc.) to the body and facilitates the movement of the peripheral. As such, the nodes include wrists, elbows, shoulders, neck, knees, ankles, etc. When performing a task subjects a node to a force or stress point, a sensor 202 should be attached thereto. Although FIG. 2 shows nine sensors 202 attached to nine nodes, this number can be larger or smaller depending on the type of work. For example, when a work shift moves upper body nodes only (e.g., the worker sits during the work shift at a work bench and uses his or her hands and arms to assemble parts), the number of sensors can be reduced since there is no need to collect data about the lower body nodes that are supposed to be more or less stationary.

Various attachment means can be used to attach and secure a sensor 202 to a node. For example, the sensor 202 uses a fabric hook and loop fastener strap, e.g., commercially available from Velcro®, to tightly wrap around the node. Alternatively, the sensor 202 may be integrated with an outfit of the subject such that it overlays the node. For example, the sensor 202 is glued or sewn to the outfit or is installed in a pocket at a location of the node.

In comparison, the central computing unit 204 need not be attached to a node or the body of the subject. For example, the subject can attach the central computing unit 204 to a waist belt, put it in a side pocket of the outfit, or leave it on a structure in proximity to a location of a work task. The central computing unit 204 can interface wirelessly with the sensors 202 (e.g., by way of wireless personal area networks such as Bluetooth®, infrared, etc.), but can also use a wired connection. Also, as explained above, the central computing unit 204 interfaces with the processing center 104 by way of the access point 106 or a wired connection. However, in an example, an intermediary device can also be used. For example, the central computing unit 204 interfaces with a smartphone, a tablet, or another computing device that, in turn, provides data received from the central computing unit 204 to the processing center 104.

Various data can be measured with regard to each node including, for example, posture, motion, orientation, position, force, velocity, acceleration, jerk, vibration, noise, etc. Thus, each sensor 202 can include various types of sensors and devices such as a combination of an accelerometer such as a three-dimensional accelerometer, gyroscope, inclinometer, location sensor, position sensor, tilt sensor, rotation sensor, motion sensor, environmental sensor, temperature sensor, barometric pressure sensor, compass/gravity sensor, magnetic sensor, etc. The sensor 202 can also be implemented as a virtual sensor that combines measurement and functionalities of the various types of sensors and devices. To illustrate a use of a sensor to measure a certain type of data, an accelerometer attached to a node can be used to measure acceleration data at the node. The amplitude of the acceleration data is indicative of a force applied to the node. If the acceleration data indicates that the force alternates directions, this alternation is indicative of a vibration at the node. Changes in the acceleration data also indicate a jerk movement at the node. Additionally or alternatively, the accelerometer can measure position data such as an origin or neutral position and travelled positions. The travelled positions can be processed to determine movements and distances that the node travelled relative to the neutral position. Likewise, frequencies and directions associated with changes between travelled positions and the neutral position can be processed to determine vibrations and directions of the forces associated with the vibrations. Those skilled in the art will appreciate that various data can be measured by the sensors 202 depending on the node that each sensor is attached to and the movements that the node is experiencing.

The sensors 202 transmit the measured data to the central computing unit 204 that in turn processes to determine the movements at each node. For example, to drill holes in a surface, a subject operates a drill tool that repetitively applies vibrating forces to that subject's arms. Thus, the sensors 202A and 202E attached to the wrists detect these forces. Similarly, to lift an object, the worker quickly accelerates a node (e.g., shoulders, wrists, etc.) and/or applies forces to the node. Thus, the sensors 202B and 202D attached to the shoulders and the sensors 202A and 202E attached to the wrists measure the corresponding data.

In an example, the central computing unit 204 adds time and location stamps to the processed data. The time is usually measured by way of a clock operated by the central computing unit 204, while the location is either available from the measured data or from a location sensor of the central computing unit 204 (e.g., circuitry that determines coordinates based on global positioning system (GPS), location triangulation techniques, etc.).

Additionally, the central computing unit 204 can label the processed data to identify the corresponding nodes. For example, a label of "LW" is added to data measured by the sensor 202A to indicate that this data is associated with the left wrist attached to this sensor. Further, the central processing unit 204 can categorize the data into a type of movement such as kneeling, lifting, bending, pulling, pushing, overhead operation, hand/arm motions, etc. This categorization can combine the data from several sensors 202. For example, data measured by the sensors 202F and 202G attached to the knees are combined to represent kneeling movements as applicable. Similarly, data measured by the sensors 202A, 202B, 202C, 202D, and 202E attached to the wrists, shoulders, and neck are combined to represent lifting movements as applicable.

Moreover, the central computing unit 204 can correlate the data (e.g., the time and location stamped, labeled, and categorized data) with a corresponding task(s) of the subject. For example, the central computing unit 204 can have access to a database that lists the tasks of a work shift and their times. This database can be a component of the processing center 104 or can be locally stored at the central computing unit 204. Based on the time when the data is measured, the central computing unit 204 retrieves the corresponding task from the database and correlates it to the data. In another example, the central computing unit 204 can provide a user interface to the subject. In turn, if the subject enters an identifier of the task (e.g., a task number, a task title, etc.) at the user interface shortly before performing it, the central computing unit 204 associates the identifier with the data.

Additionally, the central computing unit 204 can also add an identifier of the subject (e.g., name, title, employee number, etc.) to the data to allow the processing center 104 and/or the ergonomist (not shown) to identify the subject in order to provide him or her with a service (e.g., the processing center 104 sending an alert to the wearable computing unit 102 of the subject to alert of potential discomfort, the ergonomist having a discussion with the worker, etc.). However, for privacy reasons the data can also be made anonymous. As such, the central computing unit 204 removes any data that identifies the subject before transmission to the processing center 104. But to receive a service back from the processing center (e.g., an alert), the central computing unit 204 generates an identifier (e.g., a random number) that identifies it to the processing center 104. Thus, the processing center 104 tracks the data collected over time and provides a service to the central computing unit 204 based on an identifier of the central computing unit 204 rather than the subject.

As explained above, the wearable computing unit 102 can notify the subject of hot spots through various sensory signals (e.g., audible sound, a text, a flashing light, a vibration, etc.). Thus, in addition to processing and transmitting the data, the central computing unit 204 can also provide an interface for monitoring the hot spots. For example, the central computing unit 204 is configured with various circuitries to generate the sensory signals (e.g., a speaker, a monitor, a LED light, a vibration mechanism, etc.).

Figure 3:
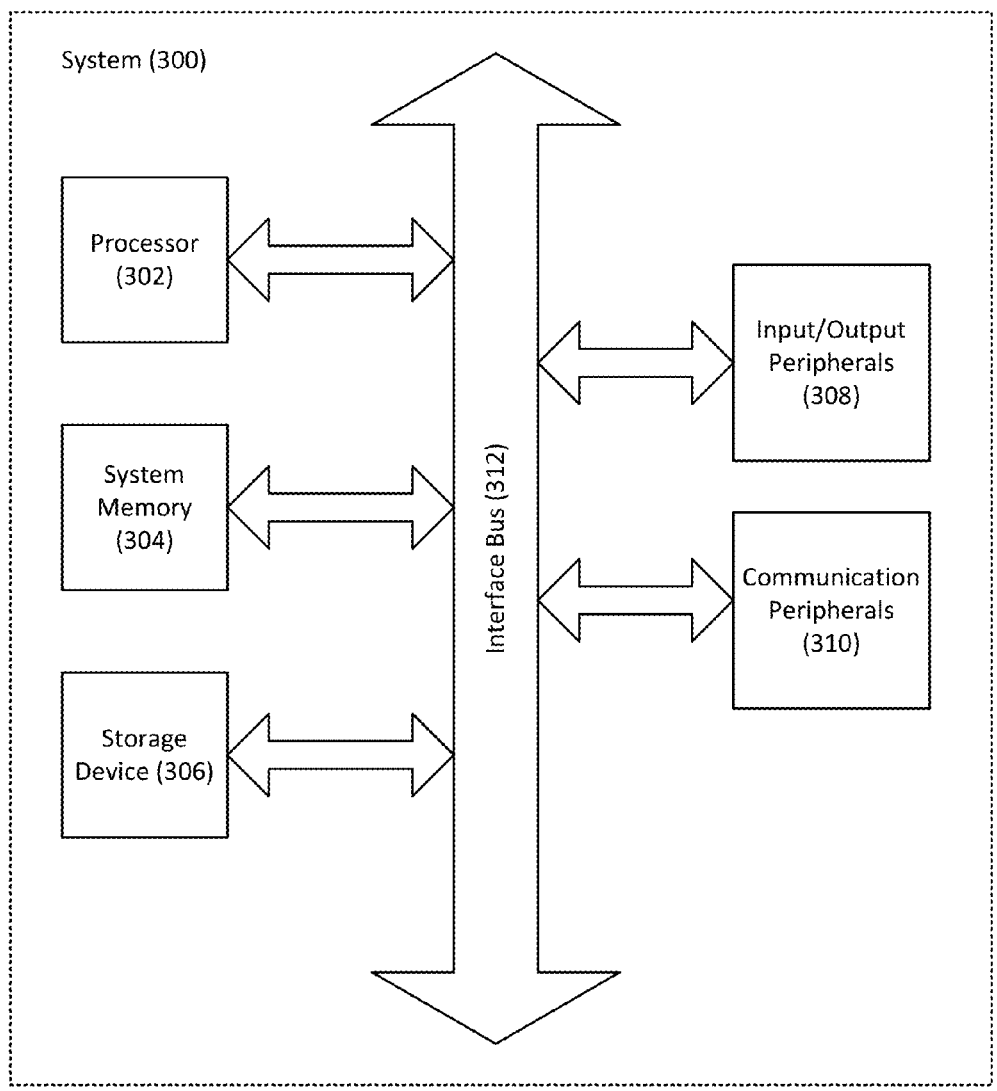
FIG. 3 is an illustration of an example circuitry of a computing system for monitoring and improving ergonomic conditions in accordance with the disclosure.

To provide the various functionalities of the central computing units 204 and the processing center 104, some or all elements of these devices may be implemented using system 300 of FIG. 3. More particularly, FIG. 3 illustrates an example of circuitry for implementing the monitoring and detecting techniques in accordance with the present disclosure. As used herein, the term "circuitry" includes hardware components (e.g., microprocessors, application specific integrated circuits, processors, etc.) configured using firmware and software that implement the monitoring and detecting techniques described herein. For example, a processor can be configured by instructions loaded from memory, e.g., random access memory (RAM), read-only memory (ROM), firmware, and/or mass storage, embodying logic operable to configure the processor to perform the functionalities disclosed herein. In another example, these functionalities can be implemented on a single-board microcontroller designed around a reduced instruction set computing (RISC) single chip microcontroller, for example an 8-bit RISC Atmel® AVR® or a 32-bit Atmel® ARM commercially available from Atmel® microcontroller by using a programming language compiler and a boot loader that executes on the microcontroller.

FIG. 3 illustrates an example of the system 300 that may include at least a processor 302, a system memory 304, a storage device 306, input/output peripherals 308, communication peripherals 310, and an interface bus 312. The interface bus 312 may be configured to communicate, transmit, and transfer data, controls, and commands among the various components of the system 300. The system memory 304 and the storage device 306 may comprise computer readable storage media, such as RAM, ROM, electrically erasable programmable read-only memory (EEPROM), hard-drives, CD-ROMs, optical storage devices, magnetic storage devices, electronic non-volatile computer storage, for example Flash® memory, and other tangible storage media. Any of such computer readable storage mediums can be configured to store instructions or program codes embodying aspects of the disclosure. The system memory 304 and the storage device 306 may also comprise computer readable signal media. A computer readable signal medium may include a propagated data signal with computer readable program code embodied therein. Such a propagated signal may take any of a variety of forms including, but not limited to, electromagnetic, optical, or any combination thereof. A computer readable signal medium may be any computer readable medium that is not a computer readable storage medium and that can communicate, propagate, or transport a program for use in connection with the system 300.

Further, the system memory 304 may comprise an operation system and applications. The processor 302 may be configured to execute the stored instructions and can comprise, for example, a logical processing unit, a microprocessor, a digital signal processor, and the like. The input and output peripherals 308 may include user interfaces such as a keyboard, screen, microphone, speaker, other input/output devices, and computing components such as digital-to-analog and analog-to-digital converters, graphical processing units, serial ports, parallel ports, universal serial bus, signal generators, filters, signal processors, and the like. The input/output peripherals may be connected to the processor 302 through any of the ports coupled to the interface bus 312. The communication peripherals 310 may be configured to facilitate communication between the system 300 and other computing devices over a communications network and may include, for example, a network interface controller, modem, various modulators/demodulators and encoders/decoders, wireless and wired interface cards, antenna, transmitters, receivers, and the like.

Figure 4:
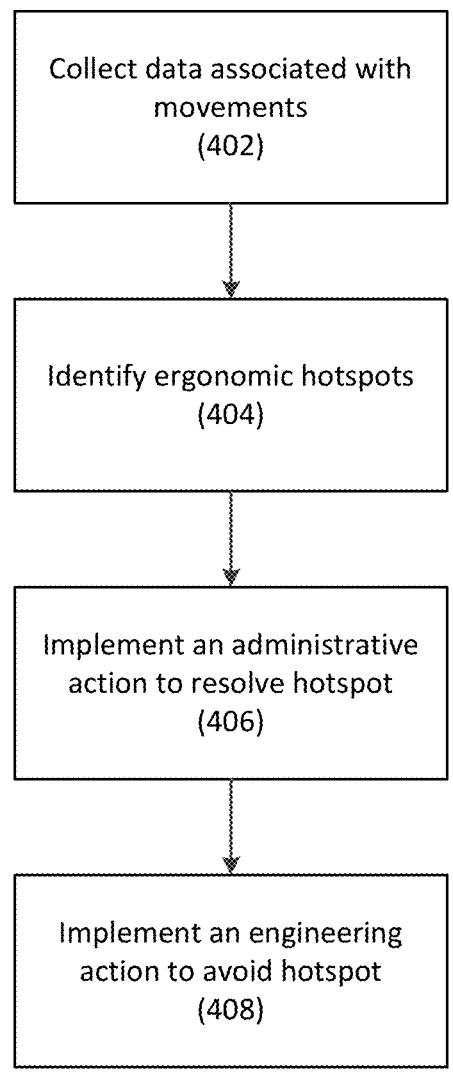
FIG. 4 is an illustration of operations for monitoring and improving ergonomic conditions in accordance with the disclosure.

Once the processing center 104 and the central computing unit 204 are configured to perform the monitoring and detecting techniques and once the sensors 202 are attached to nodes of a plurality of subjects, the various data indicative of the node movements can be collected and processed as shown in FIG. 4. The data can be analyzed in real-time to prevent physical discomfort (e.g., pains, injuries, or the like) from occurring and can be also stored for further analysis to improve the ergonomic conditions of the environment.

Operation 402 illustrates each of the wearable computing units 102 collecting and processing data from its sensors 202 and transmitting the data to the processing center 104. In turn, the processing center 104 receives, stores, and processes the data for analysis. For example, the processing center 104 aggregates the data received from the plurality of wearable computing devices 102 based on a combination of parameters, such as time, location, task, movement types, nodes, etc. To illustrate, the factory floor may include six locations corresponding to assembly stations; at least a dozen of tasks are performed by twenty-four subjects at each location within a work shift and include kneeling, lifting, bending, pulling, pushing, overhead operation, hand/arm motions; and each subject wears at least nine sensors. In other words, there are at least one hundred forty-four central computing units 104 and one thousand two hundred ninety-six sensors 202. As such, for each assembly station, the processing center 104 can track by assembly station data received from the corresponding twenty-four wearable computing units 102. Likewise, the processing center 104 can track by task data received from the one hundred forty-four wearable units across all six assembly stations. In a further example, for two assembly stations, the processing center 104 can track by the movement type data received from the corresponding forty-eight wearable computing units 102 over the first half of the work shift and can track by the node data received from these units over the second half of the work shift. Those skilled in the art will appreciate that these examples are merely illustrative and that other implementations for processing and aggregating the data are possible.

Operation 404 illustrates the processing center 104 identifying the ergonomic hot spots based on an analysis of the data. As explained herein above, the analysis includes a comparison of the data to ergonomic conditions to identify location, task, movement, and body-based ergonomic hot spots. Also, the analysis can be used to further refine the requirements of the ergonomic conditions. These ergonomic conditions can be expressed in terms of thresholds that, when exceeded, indicate hot spots.

Continuing with the previous example, one of the tasks involves installing a tire on a vehicle, which requires a kneeling movement and a hand/arm motion to fasten four nut lugs by way of a wrench activated by an air compressor. In comparison, ergonomically unacceptable conditions associated with these two movements advise against continuously kneeling for a period of one minute and for operating a tool that results in an acceleration of more than $9.81$ m/s$^2$, respectively. As such, the processing center 104 can set the one minute as a threshold for identifying a kneeling movement that uses a longer duration as hot spot. Likewise, the processing center 104 can set the $9.81$ m/s$^2$ as a threshold for identifying a force associated with operating a tool as a hot spot. If the processing center 104 detects based on the data that at the first assembly station at least six subjects continuously and repetitively knelt for more than one minute during the work shift while such movement was not detected at the remaining assembly stations, the processing center 104 declares the first assembly station as a location hot spot. Likewise, if the processing center 104 detects based on the data that the task of installing the tire commonly involves kneeling for more than one minute across the various assembly stations, the processing center 104 declares it as a task hot spot. Also, if the processing center 104 determines based on the data that the subjects are kneeling for less than a minute to install the tires but that they are commonly experiencing an acceleration in excess of $9.81$ m/s$^2$ through forces applied to their hands and arms when operating the tool, the processing center 104 declares the hands and arms as body hot spots.

Operation 406 illustrates the processing center 104 generating information indicative of an administrative action based on the declared hot spots. The administrative action can be implemented by the subjects and/or an ergonomist(s) responsible for the safety of the subjects to reduce a risk of physical discomfort. For instance, when the processing center 104 declares a hot spot, it can transmit an alert message to the subjects that are subject to the hot spot. Continuing with the example above, when a subject kneels for more than one minute, his or her wearable computing unit 102 generates an alert of a risk of knee discomfort. Based on the alert, the subject can follow a procedure set by the ergonomist to mitigate the risk. Likewise, when the processing center 104 declares a hot spot, it can display information about the hot spot at a user interface to the ergonomist who, in turn, can take corrective actions. Continuing with the previous example, the ergonomist asks the alerted subject to install two of the four lug nuts, stretch his or her legs for at least ten seconds, and then complete the installation of the two remaining lug nuts.

Operation 408 illustrates the processing center 104 generating information indicative of an engineering action based on the declared hot spots. This operation is similar to operation 406 except that it can result in an engineering solution that may redesign the configuration of the assembly stations, the flow of the work tasks, the tools used, and/or the parts that the tasks install or remove. Continuing with the previous example, when the processing center 104 declares the first assembly station as a location hot spot, the ergonomist may meet with a leader of the twenty-four subjects at that station to investigate the root cause of the problem. If the investigation indicates that a structure where the tire sits is out of specification (e.g., its level is lower than what it should be), the leader may recalibrate the structure to be within the specification and the ergonomist may further monitor the collected data to determine if the recalibration resolved the hot spot. Likewise, when the processing center 104 declares the tire installation task as a task hot spot, the ergonomist may meet with an industrial engineer and the tire engineer to resolve the hot spot. In this case, the industrial engineer may revise the installation flow to require the fastening of two lug nuts instead of four at a time. Also, the tire engineer may revise the tire design to use three lug nuts instead of four. Similarly, when the processing center 104 declares the hands and arms as body hot spots, the ergonomist may meet with a factory floor manager to discuss the use of a less vibrating tool. Those skilled in the art will appreciate that these examples are merely illustrative and that other implementations for generating administrative and engineering actions are possible.

Figure 5:
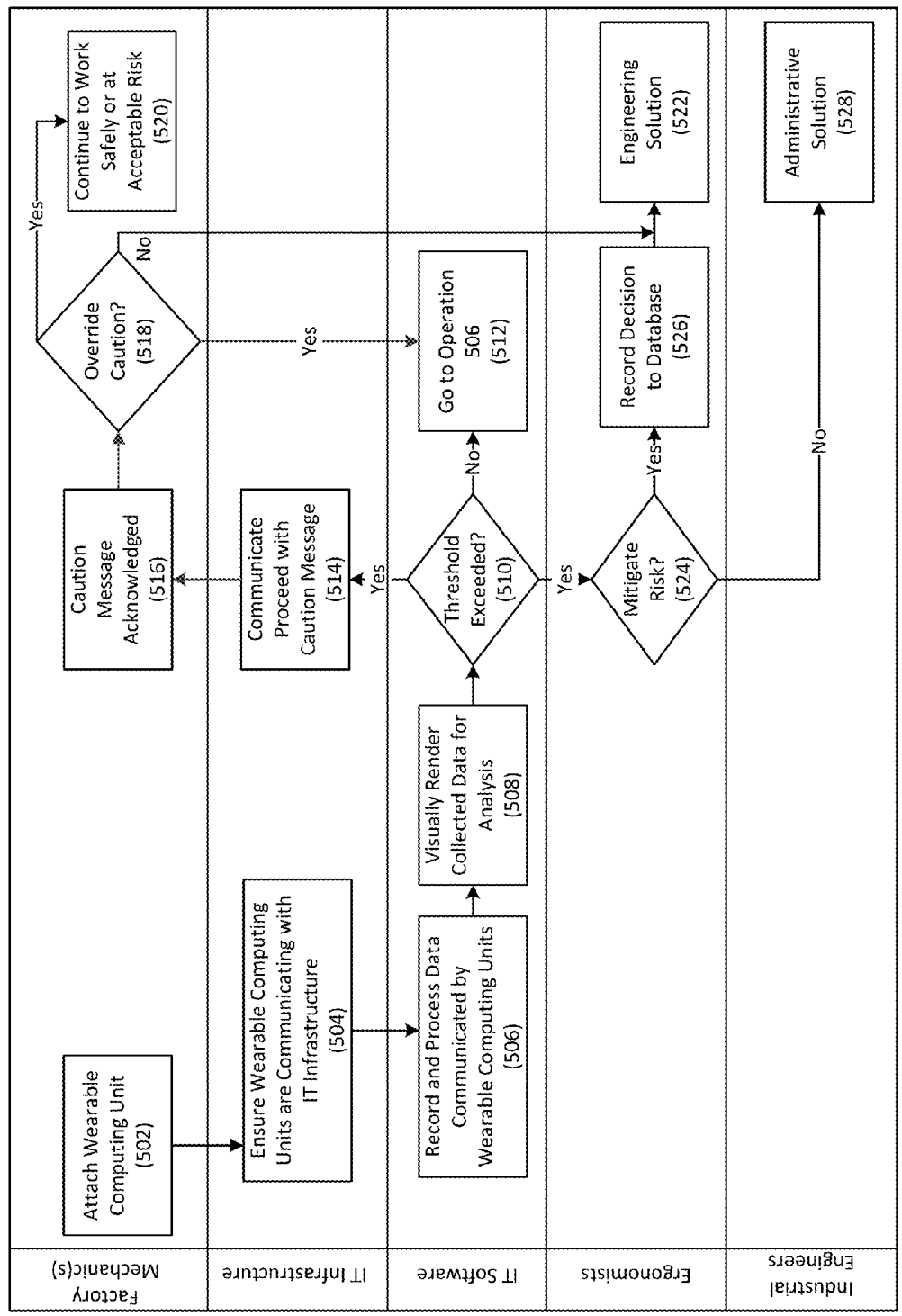
FIG. 5 is an illustration of operations performed by various groups associated with an organization to monitor and improve ergonomic conditions in accordance with the disclosure.

Turning to FIG. 5, an example operation for implementing the monitoring and detecting of ergonomic hot spots across multiple groups of an organization is illustrated. More particularly, the groups involved in implementing these techniques include a group of factory mechanics (e.g., the workers of a factory that wear the wearable computing units 102), a group that manages the information technology (IT) infrastructure (e.g., IT personnel that integrates the processing center 104 and access point 106 with an existing infrastructure of the organization), a group that manages the IT software (e.g., IT personnel that integrates the software of the wearable computing units 102 and the processing center 104 with existing software of the organization), a group of ergonomists (e.g., users of the processing center 104 that are responsible for the safety of the work environment), and a group of industrial engineers (e.g., engineers responsible for improving the work process in the factory).

Operation 502 illustrates the factory mechanics wearing the wearable computing units 102 during their work shift. Operation 504 illustrates the IT infrastructure group ensuring that the deployed wearable computing units 102 are in communication with the infrastructure, such as with the access point 106. This group troubleshoots issues that are associated with the interface between the wearable computing units 102 and the processing center 104. Operation 506 illustrates the IT software group deploying software that supports the analysis of the data collected by the processing center 104. More particularly, the deployed software allows the processing center 104 to record and process the data received from the wearable computing units 102 as described herein above. Operation 508 illustrates the IT software group configuring the processing center 104 to render visual representations of the data for analysis. This operation includes, for example, rendering the processed data by time, location, task, movement type, node, etc. Operation 510 illustrates the IT software group further configuring the processing center 104 to compare the data to a threshold (e.g., the ergonomically unacceptable conditions) to determine if a hot spot exists. An example illustrating operations 508 and 510 is further described in FIG. 6. If a hot spot does not exist, operation 512 follows operation 510. Otherwise, operations 514 and 524 follow operation 510. In operation 512, the IT software group configures the processing center to keep recording, processing, rendering, and analyzing the data by performing operations 506-510.

Operation 514 illustrates that a hot spot is detected triggering the processing center 104 to transmit a caution message to the wearable computing units 102 of the impacted factory mechanics prior to an occurrence of physical discomfort related to the hot spot. Operation 516 illustrates the impacted factory mechanics acknowledging the caution message. For example, the message is displayed at a user interface of the wearable computing units 102 and is acknowledged by a click of dedicated hard or soft buttons on the wearable computing units 102, which in turn generates an acknowledgement message. Operating 518 illustrates each impacted mechanic deciding whether he or she wants to override the caution message. If the caution message is overridden, operation 520 is performed and illustrates the mechanic continuing with his or her work. Also if the caution message is overridden, operation 512 may be performed. For example, the mechanic can change the performance of a task to be more comfortable, safer, or to be at an acceptable risk. If the caution message is not overridden, operation 522 is performed. Operation 522 illustrates the ergonomists taking engineering solutions to reduce the risks of injury.

In parallel to operation 514, operation 524 follows operation 510 when a hot spot is identified. Operation 524 illustrates the ergonomists deciding whether the risk of physical discomfort should be mitigated by way of engineering solutions. If an engineering solution is to be implemented, operation 526 is followed and illustrates the ergonomists recording the solutions in a database. This database can be accessible to the processing center 104 such that the processing center 104 can refine the requirements of the ergonomic conditions. The ergonomists also implement the engineering solutions as illustrated in operation 522. If engineering solutions are not performed, administrative solutions can be implemented as illustrated in operation 528. This operation can be performed by the industrial engineers who redesign the configuration of the factory floor, the task flow, the tools, or the parts to reduce the risks of physical discomfort.

The various operations illustrated in FIG. 5 need not be limited to the groups identified in FIG. 5 and/or may also be distributed among these groups in a different order. For example, operation 522 (engineering solution) may be carried out by the industrial engineers instead of the ergonomists. Alternatively, the ergonomists may be responsible for this operation but may be able to delegate its execution to an engineer, a factory manager, a supplier, etc.

A feature that can be implemented at the processing center 104 is the visualization of the processed data and their comparisons to thresholds (e.g., acceleration thresholds) to detect hot spots. This feature allows the ergonomist to get visual snapshots representative of the cumulative effect of the forces, motions, postures, etc., that the subjects experience over time and the associated ergonomic hot spots. An example of this feature is shown in FIG. 6, which illustrates a visualization of the data by movement type (e.g., bending, hand/arm motion, kneeling, lifting, overhead motion, push/pull motion, etc.) for an individual subject over two work days. However, those skilled in the art will appreciate that other visualizations of the data may be implemented. For example, the visualized data can be associated with a plurality of subjects, over longer or shorter time periods. Also the visualized data can be shown by hot spot type (e.g., location, task, movement, body), by node, etc. The data can be rendered on a monitor or a display accessible to the ergonomist.

FIG. 6 illustrates the time period as the horizontal axis and shows a work shift that starts at 6:00 am and ends at 2:00 pm. This figure also illustrates a list of movement types on the vertical axis. As the subject starts performing tasks during his or her work shift, the measured data can be cumulatively added over time for each movement type. Also for each movement type, the cumulative data can be compared to the applicable ergonomically unacceptable conditions. These conditions can be visualized as threshold areas.

For example, considering the overhead motion type, the applicable ergonomically unacceptable conditions advise that no more than two hundred pounds of weight can be held overhead in an eight-hour work shift (e.g., while installing parts in a vehicle that is located at a position higher than the subject—the subject may need to lift the part and the tools to install it). This condition may be visualized with a shaded area, shown as suggested threshold 602 in FIG. 6. In comparison, the tracked data is indicative of the load that the wrists and shoulders of the subject experienced while performing overhead activities. As this data is cumulatively added and visualized, the visualization indicates that at 8:00 am of the first day, the overhead threshold (e.g., the total of two hundred pounds) was exceeded (shown as "suggested threshold exceeded 604" in FIG. 6). However, on that first day no subsequent overhead motion was detected. This can be in response to an alert sent to the wearable computing unit 102 of the subject who, in turn, acknowledged the alert and decided to avert any additional overhead activities. In comparison, on the second day, the overhead threshold was reached within the first work hour (shown as "suggested threshold exceeded 606" in FIG. 6). But in this case, the subject decided to override the alert message and continued to perform overhead activities as shown by the increase of the tracked overhead data after the first work hour.

As shown also in FIG. 6, when a hot spot is identified (e.g., the cumulative data of a movement type exceeds the corresponding threshold), the location and task associated with the hot spot (shown as Location ABC and Task No. 123 in FIG. 6) can also be visualized. This allows the ergonomist to further analyze the data to understand the root cause of the hot spot. Additionally, the visualization of the location, task, and data in general, can be configured and customized based on the needs of the ergonomist. For example, the ergonomist can request by way of an interface at the processing center 104 to show all tasks associated with the movement types, to show data of one movement type, to expand the tracked period of time, etc.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. The example systems and components described herein may be configured differently than described. For example, elements may be added to, removed from, or rearranged compared to the disclosed examples.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Similarly, the term "at least one of" is used in its inclusive sense (and not in its exclusive sense) so that when used, for example, in reference with a list of elements, the term "at least one of" means one, some, or all of the elements in the list rather than one of each element and/or one from each category or type of elements.

While certain examples have been described, these examples have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed:

1. A method for monitoring performance of a process, the method comprising:
   receiving acceleration data from wearable nodes, the acceleration data being indicative of movements of the wearable nodes as a person wearing the wearable nodes is engaged in movement associated with a defined and repeatable task, wherein an amplitude of the acceleration data is indicative of a force detected at the wearable nodes;
   accumulating the received acceleration data;
   analyzing the accumulated acceleration data by comparing the accumulated acceleration data to one or more acceleration thresholds;
   determining, based on the analyzing, a pattern of task-related movements indicative of ergonomically unacceptable conditions for the defined and repeatable task;

identifying an ergonomic hot spot based at least in part on the pattern of task-related movements and associating the identified ergonomic hot spot with the pattern; and sending, to a computing device that is communicatively coupled to the wearable nodes, a message of the identified ergonomic hot spot and the associated pattern of task-related movements.

2. The method of claim 1 further comprising identifying the ergonomic hot spot when acceleration data corresponding to the movements exceeds an acceleration threshold.

3. The method of claim 2 further comprising:
providing information indicative of a physical condition associated with the ergonomic hot spot, the information being provided to a subject prior to an occurrence of the physical condition; and
receiving information indicative of an acknowledgement of the physical condition from the subject.

4. The method of claim 2 further comprising providing an administrative solution to mitigate the ergonomic hot spot.

5. The method of claim 2 further comprising providing an engineering solution to mitigate the ergonomic hot spot.

6. The method of claim 1 further comprising providing a tool configured to render a cumulative effect over time of the acceleration data to a subject associated with the nodes and an identifier of an ergonomic hot spot associated with the acceleration data.

7. A system comprising:
a first wearable computing device comprising a first accelerometer, the first wearable computing device configured to collect acceleration data caused by movements by a person wearing the first wearable computing device; and
a second computing device communicatively coupled to the first computing device, the second computing device configured to:
receive the acceleration data from the first wearable computing device as a person wearing the wearable computing device is engaged in movement associated with a defined and repeatable task, wherein an amplitude of the acceleration data is indicative of a force detected at the first wearable computing device;
accumulate the received acceleration data;
process the received and accumulated acceleration data and one or more thresholds to determine a pattern of task-related movements indicative of an ergonomically unacceptable condition;
identify an ergonomic hot spot based at least in part on the pattern of task-related movements for the defined and repeatable task and associate the identified ergonomic hot spot with the pattern of task-related movements; and
generate a warning indicative of the identified ergonomic hot spot and the associated pattern of task-related movements.

8. The system of claim 7, wherein the second computing device is further configured to associate a set of the received data with the ergonomic hot spot when the received and accumulated acceleration data corresponding to the one of the movements exceeds an acceleration threshold from the one or more thresholds.

9. The system of claim 8, wherein the first wearable computing device comprises a second accelerometer, wherein:
the first accelerometer is attached to a first node;
the second accelerometers is attached to a second node;
the first node is different from the second node; and
the acceleration data comprises data measured by the first accelerometer and the second accelerometer.

10. The system of claim 9, wherein the second computing device is configured to associate the first node or the second node with the ergonomic hot spot based at least in part on a comparison of the acceleration data associated with the first accelerometer and the second accelerometer to the one or more thresholds.

11. The system of claim 8, further comprising a plurality of wearable computing devices comprising accelerometers, the plurality of wearable computing devices configured to be attached to a plurality of subjects and collect acceleration data caused by movements associated with the plurality of subjects.

12. The system of claim 11, wherein the second computing device is further configured to analyze collected acceleration data to determine that a task associated with the plurality of subjects is an ergonomic hot spot.

13. The system of claim 11, wherein the second computing device is further configured to analyze the collected acceleration data to determine that a location within a work environment associated with the plurality of subjects is an ergonomic hot spot.

14. The system of claim 11, wherein the second computing device is further configured to analyze the collected acceleration data to determine that a set of movements associated with the plurality of subjects is an ergonomic hot spot.

15. The system of claim 7, wherein the acceleration data is indicative of a vibration movement associated with a subject, the first computing device being attached to the subject.

16. The system of claim 7, wherein a change in the acceleration data is indicative of a jerk movement associated with a subject, the first computing device being attached to the subject.

17. A non-transitory computer readable storage medium comprising computer readable instructions that, when executed on a system comprising a processor and memory, cause the system to at least:
receive data indicative of physical movements of a plurality of subjects by way of a plurality of wearable devices attached to the plurality of subjects, wherein an amplitude of the data is indicative of a force detected at the wearable devices;
accumulate the received data;
analyze at least a subset of the accumulated data by comparing the subset of the data to one or more thresholds;
determine, based on the analyzed subset, a pattern of task-related movements indicative of an ergonomically unacceptable condition for a defined and repeatable task;
identify an ergonomic hot spot based at least in part on the pattern of task-related movements and associate the identified ergonomic hot spot with the pattern; and
send, to one of the wearable devices, a message of the identified ergonomic hot spot and the associated pattern of task-related movements.

18. The computer readable storage medium of claim 17 comprising further computer readable instructions that, when executed on the system, cause the system to at least determine that the ergonomic hot spot meets a specified ergonomic condition.

19. The computer readable storage medium of claim 18, wherein the data indicative of the physical movements further comprise a combination of motion data, posture data, and location data, the motion data comprising vibration data and force data.

20. The computer readable storage medium of claim 18, wherein the ergonomic condition is updated based at least in part on the data indicative of the physical movement.

21. The method of claim 1, wherein the ergonomic hot spot is indicative of repetitive or continuous task-related movements.

\* \* \* \* \*